US006884794B2

(12) United States Patent  (10) Patent No.: US 6,884,794 B2
Staniforth et al.  (45) Date of Patent: Apr. 26, 2005

(54) PHARMACEUTICAL FORMULATIONS FOR DRY POWDER INHALERS IN THE FORM OF HARD-PELLETS

(75) Inventors: John Nicholas Staniforth, Parma (IT); David Alexander Vodden Morton, Parma (IT); Rajbir Gill, Parma (IT); Gaetano Brambilla, Parma (IT); Rossella Musa, Parma (IT); Lorenzo Ferrarini, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 10/257,368

(22) PCT Filed: Apr. 17, 2001

(86) PCT No.: PCT/EP01/04338

§ 371 (c)(1),
(2), (4) Date: Feb. 4, 2003

(87) PCT Pub. No.: WO01/78693

PCT Pub. Date: Oct. 25, 2001

(65) Prior Publication Data

US 2003/0180227 A1 Sep. 25, 2003

(30) Foreign Application Priority Data

Apr. 17, 2000 (GB) .............................. 0009469
Jun. 27, 2000 (EP) .............................. 00113608

(51) Int. Cl.[7] .................. A61K 31/56; A61K 31/58; A61K 31/47; A61K 31/135; A61K 9/16
(52) U.S. Cl. .................. 514/170; 514/171; 514/174; 514/178; 514/311; 514/654; 424/489; 424/493
(58) Field of Search .................. 514/174, 311, 514/654, 170, 171, 178; 424/489, 490, 493

(56) References Cited

U.S. PATENT DOCUMENTS

| | | | |
|---|---|---|---|
| 6,521,260 B1 | 2/2003 | Staniforth | |
| 6,528,096 B1 | 3/2003 | Musa et al. | |
| 6,645,466 B1 | 11/2003 | Keller et al. | |
| 2003/0133880 A1 | 7/2003 | Musa et al. | |

FOREIGN PATENT DOCUMENTS

| | | |
|---|---|---|
| CA | 2 347 856 | 5/2000 |
| EP | 0 239 798 | 10/1987 |
| EP | 0 441 740 | 8/1991 |
| EP | 0 606 486 | 7/1994 |
| GB | 1242211 | 8/1971 |
| GB | 1381872 | 1/1975 |
| GB | 1520247 | 8/1978 |
| GB | 1571629 | 7/1980 |
| WO | WO 87/05213 | 9/1987 |
| WO | WO 93/11746 | 6/1993 |
| WO | 95 11666 | 5/1995 |
| WO | WO 95/24889 | 9/1995 |
| WO | WO 96/02231 | 2/1996 |
| WO | 96 23485 | 8/1996 |
| WO | WO 98/31351 | 7/1998 |
| WO | WO 98/31353 | 7/1998 |
| WO | 00 28979 | 5/2000 |
| WO | WO 00/33789 | 6/2000 |
| WO | WO 00/53157 | 9/2000 |

OTHER PUBLICATIONS

D. Ganderton, J. Pharm. Pharmac., vol. 21, pp. 9S–18S (1969).
K.S. Murthy et al, J. Pharmaceutical Sciences, vol. 66, pp. 1215–1219 (1977).
H.M. Mahmoud et al, Acta Pharm. Fenn., vol. 94, pp 125–131 (1985).
Z.T. Chowhan et al, J. Pharmaceutical Sciences, vol. 75, pp. 534–541 (1986).
H.V. van Kamp et al, Pharm. Acta Helv., vol. 61, pp. 22–29 (1986).
N.M. Kassem, Thesis, pp. 188–213 (1990).
Remington's Pharmaceutical Sciences, 18th Ed., A.R. Gennaro, Ed., Mack Publishing Co., Easton, PA, pp. 589, 593, 602, 1451, 1452, 1633, 1636, 1637 (1990).
D. Ganderton et al., Advances in Pharmaceutical Sciences, Academic Press, pp. 165–191 (1992).
J. Peart et al, Pharmaceutical Research, vol. 14, No. 11, Nov. 1997 (Supplement), 1997 AAPS Annual Meeting, Contributed Papers, Abstracts, Boston, MA, Nov. 2–6, 1997, Abstract No. 1405.
Hancock, et al., J. Pharm. Sci., vol. 86, pp. 1–12 (1997).
X. M. Zeng, et al., Int J. Pharmaceutics, vol. 176, pp. 99–110 (1998).
S. Malamataris, Powder Technol., vol. 28, pp. 35–42 (1981).
Lindberg, Acta Pharm., Suecica, pp. 207–214 (1972).
H. Lieberman, et al., Pharmaceutical Dosage Forms, Dekker, pp. 77–85 (1998).
H.A. Lieberman, et al., "Pharmaceutical Dosage Forms", Marcel Dekker, Inc., pp. 77–85, 1981.

Primary Examiner—Raymond J. Henley, III
(74) Attorney, Agent, or Firm—Oblon, Spivak, McClelland, Maier & Neustadt, P.C.

(57) ABSTRACT

The invention provides a formulation to be administered as dry powder for inhalation suitable for efficacious delivery of active ingredients into the low respiratory tract of patients suffering of pulmonary diseases such as asthma. In particular, the invention provides a formulation to be administered as dry powder for inhalation freely flowable, which can be produced in a simple way, physically and chemically stable and able of delivering either accurate doses and high fine particle fraction of low strength active ingredients by using a high- or medium resistance device.

32 Claims, No Drawings

PHARMACEUTICAL FORMULATIONS FOR DRY POWDER INHALERS IN THE FORM OF HARD-PELLETS

PRIOR ART

Inhalation anti-asthmatics are widely used in the treatment of reversible airway obstruction, inflammation and hyperresponsiveness.

Presently, the most widely used systems for inhalation therapy are the pressurised metered dose inhalers (MDIs) which use a propellant to expel droplets containing the pharmaceutical product to the respiratory tract.

However, despite their practicality and popularity, MDIs have some disadvantages:
i) droplets leaving the actuator orifice could be large or have an extremely high velocity resulting in extensive oropharyngeal deposition to the detriment of the dose which penetrates into the lungs; the amount of drug which penetrates the bronchial tree may be further reduced by poor inhalation technique, due to the common difficulty of the patient to synchronise actuation form the device with inspiration;
ii) chlorofluorocarbons (CFCs), such as freons contained as propellants in MDIs, are disadvantageous on environmental grounds as they have a proven damaging effect on the atmospheric ozone layer.

Dry powder inhalers (DPIs) constitute a valid alternative to MDIs for the administration of drugs to airways. The main advantages of DPIs are:
i) being breath-actuated delivery systems, they do not require co-ordination of actuation since release of the drug is dependent on the patient own inhalation;
ii) they do not contain propellants acting as environmental hazards;
iii) the velocity of the delivered particles is the same or lower than that of the flow of inspired air, so making them more prone to follow the air flow than the faster moving MDI particles, thereby reducing upper respiratory tract deposition.

DPIs can be Divided into Two Basic Types:
i) single dose inhalers, for the administration of pre-subdivided single doses of the active compound;
ii) multidose dry powder inhalers (MDPIs), either with pre-subdivided single doses or pre-loaded with quantities of active ingredient sufficient for multiple doses; each dose is created by a metering unit within the inhaler.

On the basis of the required inspiratory flow rates (1/min) which in turn are strictly depending on their design and mechanical features, DPI's are also divided in:
i) low-resistance devices (>90/min);
ii) medium-resistance devices (about 60 1/min);
iii) high-resistance devices (about 30 1/min).

The reported flow rates refer to the pressure drop of 4 KPa (KiloPascal) in accordance to the European Pharmacopoeia (Eur Ph).

Drugs intended for inhalation as dry powders should be used in the form of micronised powder so they are characterised by particles of few microns ($\mu m$) particle size. Said size is quantified by measuring a characteristic equivalent sphere diameter, known as aerodynamic diameter, which indicates the capability of the particles of being transported suspended in an air stream. Hereinafter, we consider as particle size the mass median aerodynamic diameter (MMAD) which corresponds to the aerodynamic diameter of 50 percent by weight of the particles. Respirable particles are generally considered to be those with diameters from 0.5 to 6 $\mu m$, as they are able of penetrating into the lower lungs, i.e. the bronchiolar and alveolar sites, where absorption takes place. Larger particles are mostly deposited in the oropharyngeal cavity so they cannot reach said sites, whereas the smaller ones are exhaled.

Although micronisation of the active drug is essential for deposition into the lower lungs during inhalation, it is also known that the finer are the particles, the stronger are the cohesion forces. Strong cohesion forces hinder the handling of the powder during the manufacturing process (pouring, filling). Moreover they reduce the flowability of the particles while favouring the agglomeration and/or adhesion thereof to the walls. In multidose DPI's, said phenomena impair the loading of the powder from the reservoir to the aerosolization chamber, so giving rise to handling and metering accuracy problems.

Poor flowability is also detrimental to the respirable fraction of the delivered dose being the active particles unable to leave the inhaler and remaining adhered to the interior of the inhaler or leaving the inhaler as large agglomerates; agglomerated particles, in turn, cannot reach the bronchiolar and alveolar sites of the lungs. The uncertainty as to the extent of agglomeration of the particles between each actuation of the inhaler and also between inhalers and different batches of particles, leads to poor dose reproducibility as well.

In the prior art, one possible method of improving the flowing properties of these powders is to agglomerate, in a controlled manner, the micronised particles to form spheres of relatively high density and compactness. The process is termed spheronisation while the round particles formed are called pellets. When, before spheronisation, the active ingredient is mixed with a plurality of fine particles of one or more excipient, the resulting product has been termed as soft pellets.

Otherwise powders for inhalation could be formulated by mixing the micronised drug with a carrier material (generally lactose, preferably $\alpha$lactose monohydrate) consisting of coarser particles to give rise to so-called 'ordered mixtures'.

However, either ordered mixtures and pellets should be able to effectively release the drug particles during inhalation, in order to allow them to reach the target site into the lungs.

At this regard, it is well known that the interparticle forces which occur between the two ingredients in the ordered mixtures may turn out to be too high thus preventing the separation of the micronised drug particles from the surface of the coarse carrier ones during inhalation. The surface of the carrier particles is, indeed, not smooth but has asperities and clefts, which are high energy sites on which the active particles are preferably attracted to and adhere more strongly. In addition, ordered mixtures consisting of low strength active ingredients could also face problems of uniformity of distribution and hence of metering accurate doses.

On the other hand, soft pellets may reach a so high internal coherence as to compromise their breaking up into the small particles during inhalation; such drawback could be regarded as a particular critical step when high-resistance dry powder inhalers are used. With said inhalers, less energy is indeed available for breaking up the pellets into the small primary particles of the active ingredient. The soft pellets may also face some problems of handling during filling and use of the inhalers.

In consideration of all problems and disadvantages outlined, it would be highly advantageous to provide a formulation aimed at delivering low strength active ingredients after inhalation with a DPI device, preferably a high-resistance one and exhibiting: i) good uniformity of distribution of the active ingredient; ii) small drug dosage variation (in other words, adequate accuracy of the delivered doses); iii) good flowability; iv) adequate physical stability in the device before use; v) good performance in terms of emitted dose and fine particle fraction (respirable fraction).

Another requirement for an acceptable formulation is its adequate shelf-life.

It is known that the chemical compounds can undergo chemico-physical alterations such as amorphisation, when subjected to mechanical stresses. Amorphous or partially amorphous materials, in turn, absorb water in larger amounts than crystalline ones (Hancock et al. *J. Pharm. Sci.* 1997, 86, 1–12) so formulations containing active ingredients, whose chemical stability is particularly sensitive to the humidity content, will benefit during their preparation by the use of as low as possible energy step treatment.

Therefore, it would be highly advantageous to provide a process for preparing said formulation in which a low energy step is envisioned during the incorporation of the active ingredient to the mixture in such a way to ensure adequate shelf life of the formulation suitable for commercial distribution, storage and use.

OBJECT OF THE INVENTION

It is an object of the invention to provide a formulation to be administered as a dry powder for inhalation suitable for efficacious delivery of low strength active ingredients into the low respiratory tract of patients suffering from pulmonary diseases such as asthma. In particular, it is an object of the invention to provide a formulation to be administered as a dry powder for inhalation, which is freely flowable, which can be produced in a simple way, which is physically and chemically stable and is capable of delivering either accurate does and a high fine particle fraction of the following active ingredients:

long acting β2-agonists belonging to the formula sketched below wherein R is preferably 1-formylamino-2-hydroxy-phen-5-yl (formoterol) or 8-hydroxy-2(1H)-quinolinon-5-yl (TA 2005) and its stereoisomers and their salts;

a corticosteroid selected from budesonide and its epimers, preferably its 22R epimer;

their mixture and their combination with other active ingredients such as for example beclomethasone dipropionate.

According to a first embodiment of the invention there is provided a powdery formulation comprising: i) a fraction of fine particle size constituted of a mixture of a physiologically acceptable excipient and magnesium stearate, the mixture having a mean particle size of less than 35 μm; ii) a fraction of coarse particles constituted of a physiologically acceptable carrier having a particle size of at least 90 μm, said mixture being composed of 90 to 99 percent by weight of the particles of excipient and 1 to 10 percent by weight of magnesium stearate and the ratio between the fine excipient particles and the coarse carrier particles being between 1:99 and 40:60 percent by weight; and the said mixture having been further mixed with the active ingredients mentioned above in micronised form or combination thereof.

In a preferred embodiment of the invention, the magnesium stearate particles partially coat the surface of either the excipient particles and the coarse carrier particles. Said feature could be achieved by exploiting the peculiar film forming properties of such water-insoluble additive, as also reported in the co-pending application WO 00/53157 of Chiesi. The coating can be established by scanning electron microscope and the degree of coating can be evaluated by means of the image analysis method.

It has been found indeed that the single features of adding either of a fraction with a fine particle size of the physiologically acceptable excipient or magnesium stearate is not enough for guaranteeing high fine particle doses of the aforementioned active ingredients upon inhalation in particular by a high-resistance device. For significantly improving the aerosol performances, it is necessary that both said excipient with a suitable particle size fraction should be present in the formulation and that the magnesium stearate particles should, at least partially, coat the surface of either the excipient and the coarse carrier particles.

Moreover, it has been found that the particle size of the physiologically acceptable excipient, the main component of the mixture i) is of particular importance and that the best results in terms of aerosol performances are achieved when its particle size is less than 35 μm, preferably less than 30, more preferably less than 20, even more preferably less than 15 μm.

In a more preferred embodiment, the formulation of the invention is in the form of 'hard pellets' and they are obtained by subjecting the mixture to a spheronisation process.

By the term of 'hard pellets' we mean spherical or semi-spherical units whose core is made of coarse particles. The term has been coined for distinguishing the formulation of the invention from the soft pellets of the prior art which are constituted of only microfine particles (WO 95/24889, GB 1520247, WO 98/31353).

By the term 'spheronisation' we mean the process of rounding off of the particles which occurs during the treatment.

In an even more preferred embodiment of the invention, the coarse carrier particles have a particle size of at least 175 μm as well as a highly fissured surface. A carrier of the above mentioned particle size is particularly advantageous when the fine excipient particles constitute at least the 10 percent by weight of the final formulation.

It has been found that, whereas formulations containing conventional carriers and having fine particle contents of above 10% tend to have poor flow properties, the formulations according to the invention have adequate flow properties even at fines contents (that is contents of active particles and of fine excipient particles) of up to 40 percent by weight.

The prior art discloses several approaches for improving the flowability properties and the respiratory performances of low strength active ingredients. WO 98/31351 claims a dry powder composition comprising formoterol and a carrier substance, both of which are in finely divided form wherein the formulation has a poured bulk density of from 0.28 to 0.38 g/ml. Said formulation is in the form of soft pellet and does not contain any additive.

EP 441740 claims a process and apparatus thereof for agglomerating and metering non-flowable powders preferably constituted of micronised formoterol fumarate and fine particles of lactose (soft pellets).

Furthermore several methods of the prior art were generally addressed at improving the flowability of powders for inhalation and/or reducing the adhesion between the drug particles and the carrier particles.

GB 1,242,211, GB 1,381,872 and GB 1,571,629 disclose pharmaceutical powders for the inhalatory use in which the micronised drug (0.01–10 μm) is respectively mixed with carrier particles of sizes 30 to 80 μm, 80 to 150 μm, and less than 400 μm wherein at least 50% by weight of which is above 30 μm.

WO 87/05213 describes a carrier, comprising a conglomerate of a solid water-soluble carrier and a lubricant, preferably 1% magnesium stearate, for improving the technological properties of the powder in such a way as to remedy to the reproducibility problems encountered after the repeated use of a high resistance inhaler device.

WO 96/02231 claims a mixture characterised in that the micronised active compound is mixed with rough carrier particles having a particle size of 400 μm to 1000 μm. According to a preferred embodiment of the invention, the components are mixed until the carrier crystals are coated with the fine particles (max. for 45 minutes). No example either with auxiliary additives and/or with low strength active ingredient is reported.

EP 0,663,815 claims the addition of finer particles (<10 μm) to coarser carrier particles (>20 μm) for controlling and optimising the amount of delivered drug during the aerosolisation phase.

WO 95/11666 describes a process for modifying the surface properties of the carrier particles by dislodging any asperities in the form of small grains without substantially changing the size of the particles. Said preliminary handling of the carrier causes the micronised drug particles to be subjected to weaker interparticle adhesion forces.

In WO 96/23485, carrier particles are mixed with an anti-adherent or anti-friction material consisting of one or more compounds selected from amino acids (preferably leucine); phospholipids or surfactants; the amount of additive and the process of mixing are preferably chosen in such a way as to not give rise to a real coating. It appears that the presence of a discontinuous covering as opposed to a "coating" is an important and advantageous feature. The carrier particles blended with the additive are preferably subjected to the process disclosed in WO 95/11666.

Kassem (London University Thesis 1990) disclosed the use of relatively high amount of magnesium stearate (1.5%) for increasing the 'respirable' fraction. However, the reported amount is too great and reduces the mechanical stability of the mixture before use.

WO 00/28979 is addressed to the use of small amounts of magnesium stearate as additive for improving the stability to the humidity of dry powder formulations for inhalation.

WO 00/33789 refers to an excipient powder for inhalable drugs comprising a coarse first fraction (with at least 80% by weight having a particle size of at least 10 μm), a fine second fraction (with at least 90% by weight having a particle size of no more than 10 μm) and a ternary agent which is preferably a water-soluble surface-active agent with a preference for leucine.

In none of aforementioned documents the features of the formulation of the invention are disclosed and none of the teaching therein disclosed contributes to the solution of the problem according to the invention. All the attempts of obtaining stable powder formulations of low strength active ingredients endowed of good flowability and high fine particle fraction according to some of the teaching of the prior art, for example by preparation of ordered mixture, addition of a fine fraction, mere addition of additives, were indeed unsuccessful as demonstrated by the examples reported below. In particular, in the prior art it often occurred that the solutions proposed for a technical problem (i.e. improving dispersion of the drug particles) was detrimental to the solution of another one (i.e. improving flowability, mechanical stability) or vice versa.

On the contrary, the formulation of the invention shows either excellent Theological properties and physical stability and good performances in terms of fine particle fraction , preferably more than 40%. The cohesiveness between the partners has been indeed adjusted in such a way as to give sufficient adhesion force to hold the active particles to the surface of the carrier particles during manufacturing of the dry powder and in the delivery device before use, but to allow the effective dispersion of the active particles in the respiratory tract even in the presence of a poor turbulence as that created by high-resistance devices.

Contrary to what has been stated in the prior art (EP 441740), in the formulation of the invention the presence of an additive with lubricant properties such as magnesium stearate, in a small amount, does not compromise the integrity of the pellets before use.

According to a second embodiment of the invention there are also provided processes for making the formulation of the invention, in such a way as that the magnesium stearate particles partially coat the surface of either the excipient particles and the coarse carrier particles with a degree of coating that can vary depending on the amount and particle size of the fine fraction and, in any case, is of at least 5%, preferably at least 15%.

According to a particular embodiment, there is provided a process including the steps of: i) co-micronising the excipient particles and the magnesium stearate particles such that to reduce their particle size below 35 μm, and contemporaneously making the additive particles partially coating the surface of the excipient particles; ii) spheronising by mixing the resulting mixture with the coarse carrier particles such that mixture particles adhere to the surface of the coarse carrier particles; iii) adding by mixing the active particles to the spheronised particles.

According to a further particular embodiment of the invention there is provided another process, said process including the steps of: i) mixing the excipient particles in the micronised form and the magnesium stearate particles in such a way as to make the additive particles partially coating the surface of the excipient particles; ii) spheronising by mixing the resulting mixture with the coarse carrier particles such that mixture particles adhere to the surface of the coarse carrier particles; iii) adding by mixing the active particles to the spheronised particles.

When the coarse carrier particles have a particle size of at least 175 μm and in a preferred embodiment a highly fissured surface, the formulation of the invention could also be prepared by: i) co-mixing the coarse carrier particles, magnesium stearate and the fine excipient particles for not less than two hours;

ii) adding by mixing the active particles to the mixture.

It has been indeed found that the particles need to be processed for at least two hours in order to either have a good fine particle fraction (respirable fraction) and no problem of sticking during the preparation.

In all process claimed, contrary to the prior art (WO 98/31351), the active ingredient is uniformly incorporated in the mixture by simple mixing so avoiding any potential mechanical stress which may disturb the cristallinity of its particles.

Advantageously, the coarse and fine carrier particles may be constituted of any pharmacologically acceptable inert material or combination thereof; preferred carriers are those made of crystalline sugars, in particular lactose; the most preferred are those made of α-lactose monohydrate. Advantageously the diameter of the coarse carrier particles is at least 100 µm, more advantageously at least 145 µm, preferably at least 175 µm, more preferably between 175 and 400 µm, even more preferably between 210 and 355 µm.

When the diameter of the coarse carrier particles is at least 175 µm, the carrier particles have preferably a relatively highly fissured surface, that is, on which there are clefts and valleys and other recessed regions, referred to herein collectively as fissures.

The expression "relatively highly fissured" is used herein to mean that the ratio of a theoretical envelope volume of the particles, as calculated from the envelope of the particles, to the actual volume of the particles, that is, the volume defined by the actual surface of the particles (that ratio hereafter being referred to as the "fissure index"), is at least 1.25. The theoretical envelope volume may be determined optically, for example, by examining a small sample of the particles using an electron microscope. The theoretical envelope volume of the particles may be estimated via the following method. An electron micrograph of the sample may be divided into a number of grid squares of approximately equal populations, each containing a representative sample of the particles. The population of one or more grids may then be examined and the envelope encompassing each of the particles determined visually as follows. Measure the Feret's diameter for each of the particles with respect to a fixed axis . The Feret's diameter for particles within a grid is measured relative to a fixed axis of the image, typically at least ten particles are measured for their Feret's diameter. Feret's diameter is defined as the length of the projection of a particle along a given reference line as the distance between the extreme left and right tangents that are perpendicular to the reference line. A mean Feret's diameter is derived. A theoretical mean envelope volume may then be calculated from this mean diameter to give a representative value for all the grid squares and thus the whole sample. Division of that value by the number of particles gives the mean value per particle. The actual volume of the particles may then be calculated as follows. The mean mass of a particle is calculated as follows. Take a sample of approximately 50 mg, record the precise weight to 0.1 mg . Then by optical microscopy determine the precise number of particles in that sample. The mean mass of one particle can then be determined. Repeat this five times to obtain a mean value of this mean.

Weigh out accurately a fixed mass of particles (typically 50 g), calculate the number of particles within this mass using the above mean mass value of one particle. Immerse the sample of particles in a liquid in which the particles are insoluble and, after agitation to remove trapped air, measuring the amount of liquid displaced. From this calculate the mean actual volume of one particle.

The fissure index is advantageously not less than 1.5, and is, for example, 2 or more.

An alternative method of determining whether carrier particles have appropriate characteristics is to determine the rugosity coefficient. The "rugosity coefficient" is used to mean the ratio of the perimeter of a particle outline to the perimeter of the "convex hull". This measure has been used to express the lack of smoothness in the particle outline. The "convex hull" is defined as a minimum enveloping boundary fitted to a particle outline that is nowhere concave. (See "The Shape of Powder-Particle Outlines" A. E. Hawkins, Wiley 1993). The "rugosity coefficient" may be calculated optically as follows. A sample of particles should be identified from an electron micrograph as identified above. For each particle the perimeter of the particle outline and the associated perimeter of the "convex hull" is measured to provide the "rugosity coefficient". This should be repeated for at least ten particles to obtain a mean value. The mean "rugosity coefficient" is at least 1.25.

The additive is magnesium stearate. Advantageously, the amount of magnesium stearate in the final formulation is comprised between at least 0.02 and not more than 1.5 percent by weight (which equates to 1.5 g per 100 g of final formulation), preferably at least 0.05 and not more than 1.0 percent by weight, more preferably between 0.1 and not more than 0.6 percent by weight, even more preferably between 0.2 and 0.4 percent by weight.

According to the invention the fraction with a fine particle size is composed of 90 to 99 percent by weight of the physiologically acceptable excipient and 1 to 10 percent by weight of magnesium stearate and the ratio between the fraction of fine particle size and the fraction of coarse carrier particle is comprised between 1:99 and 40:60 percent by weight, preferably between 5:95 and 30:70 percent by weight, even more preferably between 10:90 and 20:80 percent by weight.

In a preferred embodiment of the invention, the fraction with a fine particle size is composed of 98 percent by weight of α-lactose monohydrate and 2 percent by weight of magnesium stearate and the ratio between the fraction with a fine particle size and the coarse fraction made of α-lactose monohydrate particles is 10:90 percent by weight, respectively.

Advantageously the formulation of the invention has an apparent density before settling of at least 0.5 g/ml, preferably from 0.6 to 0.7 g/ml and a Carr index of less than 25, preferably less than 15.

In one of the embodiment of the invention, the excipient particles and magnesium stearate particles are co-micronised by milling, advantageously in a ball mill for at least two hours, preferably until the final particle size of the mixture is less than 35 µm, preferably less than 30 µm, more preferably less than 15 µm. In a more preferred embodiment of the invention the particles are co-micronised by using a jet mill.

Alternatively, the mixture of the excipient particles with a starting particle size less than 35 µm, preferably less than 30 µm, more preferably less than 15 µm, with the magnesium stearate particles will be prepared by mixing the components in a high-energy mixer for at least 30 minutes, preferably for at least one hour, more preferably for at least two hours.

In a general way, the person skilled in the art will select the most proper size of the fine excipient particles either by sieving or by suitably adjusting the time of co-milling.

The spheronisation step will be carried out by mixing the coarse carrier particles and the fine particle fraction in a suitable mixer, e.g. tumbler mixers such as Turbula, rotary mixers or instant mixer such as Diosna for at least 5 minutes, preferably for at least 30 minutes, more preferably for at least two hours, even more preferably for four hours. In a general way, the person skilled in the art will adjust the time of mixing and the speed of rotation of the mixer to obtain homogenous mixture.

When the formulation of the invention is prepared by co-mixing the coarse carrier particles, magnesium stearate and the fine excipient particles all together, the process is advantageously carried out in a suitable mixer, preferably in a Turbula mixer for at least two hours, preferably for at least four hours.

The ratio between the spheronised carrier and the drug (the active ingredient) will depend on the type of inhaler device used and the required dose.

The mixture of the spheronised carrier with the active particles will be prepared by mixing the components in suitable mixers like those reported above.

Advantageously, at least 90% of the particles of the drug have a particle size less than 10 $\mu$m, preferably less than 6 $\mu$m.

The process of the invention is illustrated by the following examples.

EXAMPLE 1

Hard-Pellet Formulation Containing Coarse Lactose (CapsuLac 212–355 $\mu$m), a Micronized Pre-Blend Lactose/Magnesium Stearate Mixture Obtained by Jet Milling and Formoterol Fumarate as Active Ingredient a) Preparation of the Formulation α-Lactose monohydrate SpheroLac 100 (Meggle EP D30) with a starting particle size of 50 to 400 $\mu$m (d(v, 0.5) of about 170, m) and magnesium stearate with a starting particle size of 3 to 35 $\mu$m (d(v, 0.5) of about 10 $\mu$m) in the ratio 98:2 percent by weight were co-milled in a jet mill apparatus. At the end of the treatment, a significant reduction of the particle size was observed (blend A).

85 percent by weight of α-lactose monohydrate CapsuLac (212–355 $\mu$m) was placed in a 240 ml stainless steel container, then 15 percent by weight of blend A was added. The blend was mixed in a Turbula mixer for 2 hours at 42 r.p.m (blend B).

Micronised formoterol fumarate was added to the blend B and mixed in a Turbula mixer for 10 mins at 42 r.p.m. to obtain a ratio of 12 $\mu$g of active to 20 mg of carrier; the amount of magnesium stearate in the final formulation is 0.3 percent by weight. The final formulation (hard pellet formulation) was left to stand for 10 mins then transferred to amber glass jar.

b) Characterisation of the Micronised Mixture (Blend A)

The micronized mixture (blend A) was characterised by particle size analysis (Malvern analysis), water contact angle and degree of molecular surface coating calculated according to Cassie et al. in Transaction of the Faraday Society 40; 546,1944.

The results obtained are reported in Table 1.

TABLE 1

| Micronised mixture (blend A) | |
|---|---|
| Particle size distribution ($\mu$m) | Malvern |
| d (v, 0.1) | 1.58 |
| d (v, 0.5) | 4.19 |
| d (v, 0.9) | 9.64 |
| Water contact angle | 40° |
| Degree of coating | 15% * |

* α-Lactose monohydrate water contact angle 12°; magnesium stearate water contact angle 118° c) Chemical and Technological Characterisation of the Hard-Pellet Formulation

The formulation mixture was characterised by its density/flowability parameters and uniformity of distribution of the active ingredient. The apparent volume and apparent density were tested according to the method described in the European Pharmacopoeia (Eur. Ph.). Powder mixtures (100 g) were poured into a glass graduated cylinder and the unsettled apparent volume $V_0$ is read; the apparent density before settling (dv) was calculated dividing the weight of the sample by the volume $V_0$ After 1250 taps with the described apparatus, the apparent volume after settling ($V_{1250}$) is read and the apparent density after settling (ds) was calculated.

The flowability properties were tested according to the method described in the Eur. Ph.

Powder mixtures (about 110 g) were poured into a dry funnel equipped with an orifice of suitable diameter that is blocked by suitable mean. The bottom opening of the funnel is unblocked and the time needed for the entire sample to flow out of the funnel recorded. The flowability is expressed in seconds and tenths of seconds related to 100 g of sample.

The flowability was also evaluated from the Carr's index calculated according to the following formula:

$$\text{Carr's index } (\%) = \frac{ds - dv}{ds} \times 100$$

A Carr index of less than 25 is usually considered indicative of good flowability characteristics.

The uniformity of distribution of the active ingredient was evaluated by withdrawing 10 samples, each equivalent to about a single dose, from different parts of the blend. The amount of active ingredient of each sample was determined by High-Performance Liquid Chromatpgraphy (HPLC).

The results are reported in Table 2.

TABLE 2

Chemical and Technological Parameters of the hard pellet formulation

| Apparent volume/density | |
|---|---|
| App. volume ($V_0$) before settling | 156 ml |
| App. density ($d_v$) before settling | 0.64 g/ml |
| App. volume ($V_{1250}$) after settling | 138 ml |
| App. density ($d_s$) after settling | 0.73 g/ml |
| Flowability | |
| Flow rate through 4 mm Ø | 152 s/100 g |
| Carr Index | 12 |
| Uniformity of distribution of active ingredient | |
| Mean Value | 12.1 $\mu$g |
| RSD | 2.2% | d) Determination of the Aerosol Performances.

An amount of powder for inhalation was loaded in a multidose dry powder inhaler (Pulvinal®—Chiesi Pharmaceutical SpA, Italy).

The evaluation of the aerosol performances was performed by using a modified Twin Stage Impinger apparatus, TSI (Apparatus of type A for the aerodynamic evaluation of fine particles described in FU IX, 4° supplement 1996). The equipment consists of two different glass elements, mutually connected to form two chambers capable of separating the powder for inhalation depending on its aerodynamic size; the chambers are referred to as higher (stage 1) and lower (stage 2) separation chambers, respectively. A rubber adaptor secures the connection with the inhaler containing the powder. The apparatus is connected to a vacuum pump which produces an air flow through the separation chambers and the connected inhaler. Upon actuation of the pump, the air flow carries the particles of the powder mixture, causing them to deposit in the two chambers depending on their aerodynamic diameter. The apparatus used were modified in the Stage 1 Jet in order to obtained an aerodynamic diameter limit value, dae, of 5 µm at an air flow of 30 l/min, that is considered the relevant flow rate for Pulvinal® device. Particles with higher dae deposit in Stage 1 and particles with lower dae in Stage 2. In both stages, a minimum volume of solvent is used (30 ml in Stage 2 and 7 ml in Stage 1) to prevent particles from adhering to the walls of the apparatus and to promote the recovery thereof.

The determination of the aerosol performances of the mixture obtained according to the preparation process a) was carried out with the TSI applying an air flow rate of 30 1/min for 8 seconds.

After nebulization of 10 doses, the Twin Stage Impinger was disassembled and the amounts of drug deposited in the two separation chambers were recovered by washing with a solvent mixture, then diluted to a volume of 100 and 50 ml in two volumetric flasks, one for Stage 1 and one for Stage 2, respectively. The amounts of active ingredient collected in the two volumetric flasks were then determined by High-Performance Liquid Chromatography (HPLC). The following parameters, were calculated: i) the shot weight as mean expressed as mean and relative standard deviation (RSD) ii) the fine particle dose (FPD) which is the amount of drug found in stage 2 of TSI; iii) the emitted dose which is the amount of drug delivered from the device recovered in stage 1+stage 2; iv) the fine particle fraction (FPF) which is the percentage of the emitted dose reaching the stage 2 of TSI.

The results in terms of aerosol performances are reported in Table 3.

TABLE 3

Aerosol performances

| Shot weight mg (%) | Emitted dose µg | FPD µg | FPF % |
|---|---|---|---|
| 20.0 (7.8) | 9.40 | 4.44 | 47.2 |

The formulation of the invention shows very good flow properties as demonstrated by the Carr index; this parameter is very important to obtain consistency of the delivered dose when a multi-dose dry powder inhalers with powder reservoir is used. The aerosol performance of the formulation is very good as well with about 50% of the drug reaching the stage 2 of the TSI.

EXAMPLE 2

Hard-Pellet Formulation Containing Coarse Lactose (CapsuLac 212–355 µm), a Micronized Pre-blend Lactose/Magnesium Stearate Mixture Obtained by Ball Milling and Formoterol Fumarate as Active Ingredient Blend A was prepared as described in the Example 1 but using α-lactose monohydrate SorboLac 400 with a starting particle size below 30 µm (d(v, 0.5) of about 10 µm) and carrying out the co-micronisation in a ball milling apparatus for 2 hours.

Blend B was prepared according to the Example 1 but after mixing for 6 mins and then screening through a 355 µm sieve.

The hard pellet final formulation was prepared according to the Example 1.

The particle size distribution, the water contact angle and the degree of coating for the micronized mixture (blend A), and the uniformity of distribution of the active ingredient for the final formulation (blend B), determined as previously described, are reported in Table 4.

Analogous results were achieved after preparing blend B by mixing for 4 hours without screening through a sieve.

TABLE 4

Characterisation of blends A and B

Micronised mixture (blend A)
Particle size distribution (µm) Malvern

| | |
|---|---|
| d (v, 0.1) | 0.72 µm |
| d (v, 0.5) | 2.69 µm |
| d (v, 0.9) | 21.98 µm |
| water contact angle | 52° |
| degree of coating | 25% |

Final formulation (blend B)

| | |
|---|---|
| Uniformity of distribution of the active ingredient | Mean = 11.84 µg RSD = 1.83% |

The in-vitro performances, determined as previously described, are reported in Table 5.

TABLE 5

Aerosol performances

| Shot weight mg (%) | Emitted dose µg | FPD µg | FPF % |
|---|---|---|---|
| 20.8 (6.9) | 8.57 | 4.28 | 49.9 |

As it can be appreciated from the results, also such formulation show excellent characteristics either in terms of flowability properties and in terms of aerosol performances.

EXAMPLE 3

Determination of the Suitable Amount of Magnesium Stearate to be Added in the Formulation Samples of pre-blends were prepared as described in Example 2 in a ball milling apparatus for 2 hours using α-Lactose monohydrate SorboLac 400 (Meggle microtose) with a starting particle size below 30 µm (d(v, 0.5) of about 10 µm) and magnesium stearate with a starting particle size of 3 to 35 µm (d(v, 0.5) of about 10 µm) in the ratio 98:2, 95:5 and 90:10 percent by weight (blends A).

Blends B and the hard pellet final formulation were prepared as previously described; the amount of magnesium stearate in the final formulations turns out to be 0.3, 0.75 and 1.5 percent by weight, respectively. The uniformity of distribution of active ingredient and the in-vitro aerosol performance were determined as previously described. The results obtained are reported in Table 6.

TABLE 6

Uniformity of distribution and in-vitro aerosol performances

| | Mg stearate 0.3% | Mg stearate 0.75% | Mg stearate 1.5% |
|---|---|---|---|
| Content uniformity | | | |
| Mean (µg) | 11.84 | — | — |
| RSD (%) | 1.83 | — | — |

TABLE 6-continued

Uniformity of distribution and in-vitro aerosol performances

|  | Mg stearate 0.3% | Mg stearate 0.75% | Mg stearate 1.5% |
|---|---|---|---|
| Shot weight | | | |
| Mean (mg) | 20.8 | 24.7 | 23.0 |
| RSD (%) | 6.9 | 6.5 | 2.4 |
| Emitted dose (µg) | 8.57 | 10.1 | 11.1 |
| FPD (µg) | 4.28 | 3.5 | 3.6 |
| FPF (%) | 49.9 | 35 | 32 |

In all cases, good performances in terms of fine particle dose are obtained, in particular with 0.3 percent by weight of magnesium stearate in the final formulation.

EXAMPLE 4

Ordered Mixtures Powder Formulations

Powders mixtures were prepared by mixing of commercially available α-lactose monohydrate with different particle size and formoterol fumarate to obtain a ratio of 12 µg of active to 20 mg of carrier. Blending was carried out in glass mortar for 30 mins. The uniformity of distribution of active ingredient and the in-vitro aerosol performances were determined as previously described. The results are reported In Table 7.

TABLE 7

Uniformity of distribution and in-vitro aerosol performances

|  | Spherolac 100 (63–90 µm) | Spherolac 100 (90–150 µm) | Spherolac 100 (150–250 µm) | Pharmatose 325 M (30–100 µm) |
|---|---|---|---|---|
| Content uniformity | | | | |
| Mean µg) | 11.89 | 11.81 | 12.98 | 11.90 |
| RSD (%) | 3.88 | 2.17 | 9.03 | 10.10 |
| Shot weight | | | | |
| Mean (mg) | 25.28 | 25.23 | 22.02 | 22.40 |
| RSD (%) | 7.73 | 3.39 | 6.93 | 22.00 |
| Emitted dose (µg) | 11.10 | 10.30 | 8.50 | 7.80 |
| FPD (µg) | 1.40 | 0.70 | 0.60 | 1.20 |
| FPF (%) | 12.6 | 6.8 | 7.1 | 15.4 |

The results indicate that, upon preparation of ordered mixtures containing formoterol fumarate as active ingredient according to the teaching of the prior art, the performances of the formulations are very poor.

EXAMPLE 5

Powders Formulations Containing Different Amounts of Fine Lactose Particles

Carrier A—α-Lactose monohydrate Spherolac 100 (90–150 µm) and Sorbolac 400 with a particle size below 30 µm (d(v, 0.5) of about 10 µm) in the ratio 95:5 percent by weight were mixed in a mortar for 15 mins.

Carrier B—α-Lactose monohydrate Spherolac 100 (90–150 µm) and micronised lactose (particle size below 5 µm ) in the ratio 95:5 w/w were mixed in a mortar for 15 mins.

Carrier C—α-Lactose monohydrate Spherolac 100 (150–250 µm) and Sorbolac 400 with a particle size below 30 µm (d(v, 0.5) of about 10 µm) in the ratio 95:5 percent by weight were mixed in a mortar for 30 mins.

Carrier D—α-Lactose monohydrate Spherolac 100 (150–250 µm) and Sorbolac 400 particle size below 30 µm (d(v, 0.5) of about 10 µm) in the ratio 90:10 percent by weight were mixed in a mortar for 30 mins.

In the case of all the formulations tested, the carriers were mixed with formoterol fumarate in mortar for 15 mins to obtain a ratio of 12 µg of active to 25 mg of carrier.

The results in terms of content uniformity and in-vitro aerosol performances are reported in Table 8.

TABLE 8

Content uniformity and in-vitro aerosol performances

|  | Carrier A | Carrier B | Carrier C | Carrier D |
|---|---|---|---|---|
| Content uniformity | | | | |
| Mean (µg) | 10.96 | 10.50 | 11.86 | — |
| RSD (%) | 1.80 | 15.01 | 7.10 | — |
| Shot weight | | | | |
| Mean (mg) | 23.46 | 25.29 | 25.7 | 19.53 |
| RSD (%) | 51.43 | 4.19 | 3.77 | 32.02 |
| Emitted dose (µg) | 10.40 | 9.5 | 10.1 | 5.92 |
| FPD (µg) | 1.60 | 2.3 | 2.3 | 1.30 |
| FPF (%) | 15.8 | 24.4 | 22.68 | 21.6 |

The results indicate that the performances of such formulations as well are very poor.

EXAMPLE 6

"Hard-Pellet Formulation Containing Coarse Lactose (PrismaLac 40 Fraction below 355 µm) and Fine Lactose"

α-Lactose monohydrate PrismaLac 40 with a particle size below 355 µm and Sorbolac 400 with a particle size below 30 µm (d(v, 0.5) of about 10 µm) in the ratio 60:40 percent by weight were first manually agitated for 10 mins to promote aggregation and then blended in a Turbula mixer for 30 mins at 42 r.p.m. The spheronised particles were mixed with formoterol fumarate in a Turbula mixer for 30 mins at 42 r.p.m. to obtain a ratio of 12 µg of active to 15 mg of carrier.

The results in terms of uniformity of distribution of active ingredient and in-vitro aerosol performances are reported in Table 9.

TABLE 9

Uniformity of distribution of active ingredient and in-vitro aerosol performances

|  | Spheronised particles |
|---|---|
| Content uniformity | |
| Mean (µg) | 11.90 |
| RSD (%) | 18.46 |
| Shot weight | |
| Mean (mg) | 18.10 |
| RSD (%) | 6.80 |
| Emitted dose (µg) | 11.10 |
| FPD (µg) | 2.10 |
| FPF (%) | 18.9 |

The results indicate that the formulation without magnesium stearate has very poor performance.

EXAMPLE 7

Effect of the Addition of Magnesium Stearate by Simple Mixing

Formulation A—α-Lactose monohydrate Pharmatose 325 M (30–100 µm) and magnesium stearate in the ratio 99.75:0.25 percent by weight were blended in a Turbula mixer for 2 hours at 42 r.p.m. The blend was mixed with formoterol fumarate in a Turbula mixer for 30 mins at 42 r.p.m. to obtain a ratio of 12 µg of active to 25 mg of carrier.
Formulation B—as reported above but α-Lactose monohydrate SpheroLac 100 (90–150 µm) instead of Pharmatose 325 M.
Formulation C—α-Lactose monohydrate PrismaLac 40 (with a particle size below 355 µm) and micronised lactose with a particle size below 5 µm in the ratio 40:60 percent by weight were mixed in a Turbula mixer for 60 mins at 42 r.p.m. 99.75 percent by weight of the resulting blend and 0.25 percent by weight of magnesium stearate were mixed in a Turbula mixer for 60 mins at 42 r.p.m. The resulting blend was finally mixed with formoterol fumarate in a Turbula mixer for 30 mins at 42 r.p.m. to obtain a ratio of 12 µg of active to 15 mg of carrier.
Formulation D—Sorbolac 400 with a particle size below 30 µm (d(v, 0.5) of about 10 µm) and magnesium stearate in the ratio 98: 2 percent by weight were mixed in a high shear mixer for 120 mins (blend A). 85% percent by weight α-lactose monohydrate CapsuLac (212–355 µm) and 15% percent by weight of blend A were mixed in Turbula for 2 hours at 42 r.p.m. (blend B); the amount of magnesium stearate in the final formulation is 0.3 percent by weight. Micronised formoterol fumarate was placed on the top of blend B and mixed in a Turbula mixer for 10 mins at 42 r.p.m. to obtain a ratio of 12 µg of active to 20 mg of carrier.
Formulation E—Micronized lactose with a particle size below 10 µm (d(v, 0.5) of about 3 µm) and magnesium stearate in the ratio 98: 2 percent by weight were mixed in a Sigma Blade mixer for 60 mins (blend A). 85 percent by weight of α-lactose monohydrate CapsuLac (212–355 µm) and 15 percent by weight of blend A were mixed in Turbula for 2 h at 42 r.p.m. (blend B); the amount of magnesium stearate in the final formulation is 0.3 percent by weight. Micronised formoterol fumarate was placed on the top of blend B and mixed in a Turbula mixer for 10 mins at 42 r.p.m. to obtain a ratio of 12 µg of active to 20 mg of carrier.

The results in terms of uniformity of distribution of active ingredient and in-vitro aerosol performances are reported in Table 10.

TABLE 10

Uniformity of distribution of active ingredient and in-vitro aerosol performances

|  | Formulations A | Formulations B | Formulations C | Formulations D | Formulations E |
|---|---|---|---|---|---|
| Content uniformity |  |  |  |  |  |
| Mean (µg) | 7.96 | 10.50 | 9.10 | 10.68 | 11.32 |
| RSD (%) | 2.16 | 8.30 | 24.90 | 2.80 | 3.0 |
| Shot weight |  |  |  |  |  |
| Mean (mg) | 24.10 | 26.50 | 12.50 | 22.07 | 21.87 |
| RSD (%) | 34.60 | 8.20 | 15.30 | 2.50 | 4.0 |
| Emitted dose (µg) | 6.10 | 7.60 | 9.60 | 8.60 | 9.93 |
| FPD (µg) | 0.60 | 0.90 | 1.60 | 3.38 | 4.80 |
| FPF (%) | 9.8 | 11.8 | 16.7 | 39.3 | 48.37 |

Formulations were magnesium stearate is added, by simple mixing, to the total amount of lactose (formulations A-B-C) show very poor performance; no significant differences in the performance of the formulations were observed using lactose of different particle size.

Formulations were magnesium stearate is added by a high energy mixing to a small amount of fine lactose (blend A of the formulations D and E) show a significant increase in the performances. In addition, the particle size of the fine lactose used has a significant effect on the deaggregation properties of the final formulation; in fact, formulation E prepared using a micronized lactose shows a significant improved performance compared with formulation D.

EXAMPLE 8

Effect of the Amount of Micronized Pre-Blend in the Final Formulation

αLactose monohydrate SpheroLac 100 (Meggle EP D30) with a starting particle size of 50 to 400 µm (d(v, 0.5) of about 170 µm) and magnesium stearate with a starting particle size of 3 to 35 µm (d(v, 0.5) of about 10 µm) in the ratio 98:2 percent by weight were co-milled in a jet mill apparatus (blend A) Different ratios of α-lactose monohydrate Capsulac (212–355 µm) and blend A were placed in a stainless steel container and mixed in a Turbula mixer for four hours at 32 r.p.m. (blends B)

Micronised formoterol fumarate was placed on the top of blends B and mixed in a Turbula mixer for 30 mins at 32 r.p.m. to obtain a ratio of 12 µg of active to 20 mg total mixture. The amount of magnesium stearate in the final formulation ranges between 0.05 and 0.6 percent by weight.

The results in terms of uniformity of distribution of active ingredient and in-vitro aerosol performances are reported in Table 11.

TABLE 11

Uniformity of distribution of active ingredient and in-vivo aerosol performance

|  | Ratio 97.5:2.5 | Ratio 95:5 | Ratio 92.5:7.5 | Ratio 90:10 | Ratio 80:20 | Ratio 70:30 |
|---|---|---|---|---|---|---|
| Content uniformity |  |  |  |  |  |  |
| Mean (µg) | 11.29 | 12.25 | 11.53 | 11.93 | 11.96 | 12.00 |
| RSD (%) | 3.8 | 5.7 | 1.5 | 2.5 | 2.0 | 2.0 |
| Shot weight |  |  |  |  |  |  |
| Mean (mg) | 19.27 | 20.26 | 20.38 | 21.05 | 22.39 | 22.48 |
| RSD (%) | 4.7 | 3.3 | 3.2 | 4.3 | 3.5 | 3.7 |
| Emitted dose (µg) | 10.58 | 9.20 | 10.65 | 9.18 | 9.63 | 9.88 |
| FPD (µg) | 4.18 | 5.10 | 6.78 | 5.9 | 5.33 | 5.28 |
| FPF (%) | 39.4 | 55.4 | 63.6 | 64.3 | 55.3 | 53.4 |

The results indicate that the performances of all the formulations are good.

EXAMPLE 9

Hard-Pellet Formulation Containing Coarse Lactose (CapsuLac 212–355 µm), a Micronized Pre-Blend Lactose/magnesium Stearate M by Jet Milling and Budesonide as Active Ingredient Blends A and B were prepared as described in the Example 1.

Micronised budesonide was added to the blend B and mixed in a Turbula mixer for 30 mins at 42 r.p.m. to obtain a ratio of 200 µg of active to 20 mg of carrier; the amount of magnesium stearate in the final formulation is 0.3 percent by weight. The final formulation (hard pellet formulation) was left to stand for 10 mins.

The results in terms of uniformity of distribution of active ingredient and in-vitro aerosol performances are reported in Table 12.

TABLE 12

Uniformity of distribution of active ingredient
and in-vitro aerosol performances.

| Content uniformity | |
|---|---|
| Mean (μg) | 201.60 |
| RSD (%) | 1.60 |
| Shot weight | |
| Mean (mg) | 19.47 |
| RSD (%) | 3.90 |
| Emitted dose (μg) | 178.10 |
| FPD (μg) | 71.6 |
| FPF (%) | 40.3 |

The results demonstrate that the teaching of the present invention could also be applied to the preparation of a powdery formulation of budesonide provided of good performances in term of fine particle fraction.

EXAMPLE 10

Formulation Containing Lactose 90–150 μm, a Micronized Pre-Blend Lactose/magnesium Stearate Mixture Obtained by Jet Milling and Formoterol as Active Ingredient α-Lactose monohydrate SpheroLac 100 (Meggle EP D30) with a starting particle size of 50 to 400 μm (d(v, 0.5) of about 170 μm) and magnesium stearate with a starting particle size of 3 to 35 μm (d(v, 0.5) of about 10 μm) in the ratio 98:2 percent by weight were co-milled in a jet mill apparatus (blend A).

92.5 percent by weight of α-lactose monohydrate Spherolac with a starting particle size of 90 to 150 μm (d(v, 0.5 of about 145 μm) and 7.5 percent by weight of blend A were placed in a stainless steel container and mixed in a Turbula mixer for four hours at 32 r.p.m. (blends B)

Micronised formoterol fumarate was placed on the top of blends B and mixed in a Turbula mixer for 30 mins at 32 r.p.m. to obtain a ratio of 12 μg of active to 20 mg total mixture. The amount of magnesium stearate in the final formulation is 0.15 percent by weight.

The results in terms of uniformity of distribution of active ingredient and in-vitro aerosol performances are reported in Table 13.

TABLE 13

Uniformity of distribution of active ingredient and in-vitro aerosol performances.

| Content uniformity | |
|---|---|
| Mean (μg) | 11.75 |
| RSD (%) | 1.50 |
| Shot weight | |
| Mean (mg) | — |
| RSD (%) | — |
| Emitted dose (μg) | — |
| FPD (μg) | 5.71 |
| FPF (%) | 45.2 |

From the reported results, it can be appreciated that, as long as the fraction of fine particles is less than 10 percent by weight, the performances of a formulation containing standard lactose as coarse carrier fraction and a fine particle fraction excipient obtained either by co-milling or by co-mixing, are very good.

EXAMPLE 11

Hard-Pellet Formulation Containing Coarse Lactose (CapsuLac 212–355 μm), a Micronized Pre-Blend Lactose/magnesium Stearate Mixture Obtained by Jet Milling and the Combination Formoterol/beclomethasone Dipropionate (BDP) as Active Ingredient Blends A and B were prepared as described in the Example 1.

Micronised formoterol and BDP were added to the blend B and mixed in a Turbula mixer for 30 mins at 42 r.p.m. to obtain a ratio of 12 μg and 200 μg of active, respectively, to 20 mg of carrier. The amount of magnesium stearate in the final formulation is 0.3 percent by weight. The final formulation (hard pellet formulation) was left to stand for 10 mins.

The results in terms of uniformity of distribution of the active ingredients and in-vitro aerosol performances are reported in Table 14.

TABLE 14

Uniformity of distribution of the active ingredients
and in-vitro aerosol performances.

| Content uniformity | |
|---|---|
| Mean formoterol (μg) | 11.93 |
| RSD (%) | 1.4 |
| Mean BDP (μg) | 190.0 |
| RSD (%) | 1.1 |
| FPF formoterol (%) | 47.2 |
| FPF BDP (%) | 40.4 |

The results indicate that, even in presence of a combination of active ingredients, the performances of the formulation are very good.

EXAMPLE 12

Effect of the Time of Mixing

Different blends were prepared by co-mixing CapsuLac 212–355 μm, micronized lactose with a particle size below 10 μm (d(v, 0.5) of about 3 μm) and magnesium stearate in the ratio 89.8:10:0.2 percent by weight, in a Turbula mixer (32 r.p.m.) at increasing mixing time (1, 2 and 4 hours).

Micronised formoterol fumarate was placed on the top of each blend and mixed in a Turbula mixer for 30 mins at 32 r.p.m. to obtain a ratio of 12 μg of active to 20 mg total mixture.

The results in terms of fine particle fraction (FPF) are reported in Table 15.

TABLE 15

Effect of the mixing time on FPF

| Time of mixing | Fine particle fraction (%) |
|---|---|
| 1 hour | 21.0 |
| 2 hours | 34.2 |
| 4 hours | 40.5 |

The results indicate that good performances in terms of fine particle fraction are achieved after mixing for at least two hours.

What is claimed is:

1. A medicinal powder, comprising:
   i) a fraction of fine particles, comprising particles of a physiologically acceptable excipient and particles of magnesium stearate, said fraction of fine particles having a mean particle size of less than 35 µm;

ii) a fraction of coarse particles, comprising particles of a physiologically acceptable carrier having a particle size of at least 100 µm; and iii) one or more active ingredient in micronised form selected from the group consisting of budesonide and its epimers, formoterol and its stereoisomers, TA 2005 and its stereoisomers, salts thereof, and mixtures thereof, wherein:

said fraction of fine particles (i) comprises said physiologically acceptable excipient in an amount of 90 to 99 percent by weight and said magnesium stearate in an amount of 1 to 10 percent by weight; and said fraction of fine particles and said fraction of coarse particles are present in a weight ratio of between 5:95 and 30:70.

2. A powder according to claim 1, wherein said active ingredient is the 22 R epimer of budesonide.

3. A powder according to claim 1, wherein said active ingredient is a combination of formoterol or TA-2005 with (a) a member selected from budesonide and its epimers and (b) beclomethasone dipropionate.

4. A powder according to claim 1, wherein said particles of magnesium stearate partially coat the surface of either said particles of said physiologically acceptable excipient or said particles of said physiologically acceptable carrier.

5. A powder according to claim 1, wherein said fraction of fine particles has a particle size of less than 15 µm.

6. A powder according to claim 1, wherein said particles of said physiologically acceptable carrier have a particle size of at least 175 µm, and said fraction of fine particles and said fraction of coarse particles are present in a weight ratio between 10:90 and 20:80.

7. A powder according to claim 1, wherein said particles of said physiologically acceptable carrier have a fissure index of at least 1.25.

8. A powder according to claim 1, wherein said physiologically acceptable excipient is one or more crystalline sugars.

9. A powder according to claim 1, wherein said physiologically acceptable excipient is α-lactose monohydrate.

10. A powder according to claim 1, wherein said fraction of coarse particles has a particle size of at least 175 µm.

11. A powder according to claim 1, wherein said fraction of fine particles comprises said physiologically acceptable excipient in an amount of about 98 percent by weight and said magnesium stearate in an amount of about 2 percent by weight.

12. A powder according to claim 1, wherein said fraction of fine particles and said fraction of coarse particles are present in a weight ratio between 10:90 and 20:80.

13. A powder according to claim 1, wherein said physiologically acceptable carrier comprises at least one crystalline sugar.

14. A powder according to claim 1, wherein said physiologically acceptable carrier comprises lactose.

15. A powder according to claim 1, wherein said physiologically acceptable carrier comprises α-lactose monohydrate.

16. A powder according to claim 1, wherein said magnesium stearate is present in an amount of 0.02 to 1.5% by weight, based on the total weight of said powder.

17. A powder according to claim 1, wherein said magnesium stearate is present in an amount of 0.05 to 1% by weight, based on the total weight of said powder.

18. A powder according to claim 1, wherein said magnesium stearate is present in an amount of 0.1 to 0.6% by weight, based on the total weight of said powder.

19. A powder according to claim 1, wherein said magnesium stearate is present in an amount of 0.2 to 0.4% by weight, based on the total weight of said powder.

20. A powder according to claim 1, which is prepared by a process comprising:

a) co-micronising particles of said physiologically acceptable excipient and particles of said magnesium stearate to reduce the particle size of said physiologically acceptable excipient and said magnesium stearate and to obtain a mixture in which said particles of said physiologically acceptable excipient are coated with said magnesium stearate;

b) spheronising said mixture by mixing said mixture with said particles of said physiologically acceptable carrier such that particles of said mixture adhere to the surface of said particles of said physiologically acceptable carrier, to obtain speronised particles;

c) mixing said active ingredient in micronized form with said spheronised particles.

21. A powder according to claim 20, wherein said co-micronising is carried out by milling.

22. A powder according to claim 21, wherein said milling is carried out with a jet mill.

23. A powder according to claim 1, which is prepared by a process comprising:

a) mixing in a high-energy mixer particles of said physiologically acceptable excipient having a starting particle size of less than 35 µm and particles of said magnesium stearate to obtain a mixture in which said particles of said magnesium stearate partially coat the surface of said particles of said physiologically acceptable excipient;

b) spheronising said mixture by mixing said mixture with particles of said physiologically acceptable carrier such that particles of said mixture adhere to the surface of said particles of said physiologically acceptable carrier, to obtain spheronised particles; and c) mixing said active ingredient particles in micronised form with said spheronised particles.

24. A powder according to claim 23, wherein said particles of said physiologically acceptable excipient which are mixed with said magnesium stearate have a starting particle size of less than 15 µm.

25. A powder according to claim 1, which is prepared by a process comprising:

a) co-mixing particles of said physiologically acceptable carrier, particles of said magnesium stearate and particles of said physiologically acceptable excipient, to obtain a mixture; and b) mixing said active ingredient in micronised form with said mixture, wherein said particles of said physiologically acceptable carrier have a particle size of at least 175 µm and said co-mixing is carried out for at least two hours.

26. A powder according to claim 1, which is in the form of spherical or semispherical units having a core of coarse particles.

27. A process for making a powder according to claim 1, said process comprising:

a) co-micronising particles of said physiologically acceptable excipient and particles of said magnesium stearate to reduce the particle size of said physiologically acceptable excipient and said magnesium stearate and to obtain a mixture in which said particles of said physiologically acceptable excipient are coated with said magnesium stearate;

b) spheronising said mixture by mixing said mixture with said particles of said physiologically acceptable carrier such that particles of said mixture adhere to the surface of said particles of said physiologically acceptable carrier, to obtain speronised particles; and c) mixing said active ingredient in micronized form with said spheronised particles.

28. A process according to claim 27, wherein said co-micronising is carried out by milling.

29. A process according to claim 28, wherein said milling is carried out with a jet mill.

30. A process for making a powder according to claim 1, said process comprising:

a) mixing in a high-energy mixer particles of said physiologically acceptable excipient having a starting particle size of less than 35 µm and particles of said magnesium stearate to obtain a mixture in which said particles of said magnesium stearate partially coat the surface of said particles of said physiologically acceptable excipient;

b) spheronising said mixture by mixing said mixture with particles of said physiologically acceptable carrier such that particles of said mixture adhere to the surface of said particles of said physiologically acceptable carrier, to obtain spheronised particles; and c) mixing said active ingredient in micronised form with said spheronised particles.

31. A process according to claim 30, wherein said particles of said physiologically acceptable excipient which are mixed with said magnesium stearate have a starting particle size of less than 15 µm.

32. A process of making a powder according to claim 1, said process comprising:

a) co-mixing particles of said physiologically acceptable carrier, particles of said magnesium stearate and particles of said physiologically acceptable excipient, to obtain a mixture; and b) mixing said active ingredient in micronised form with said mixture, wherein said particles of said physiologically acceptable carrier have a particle size of at least 175 µm and said co-mixing is carried out for at least two hours.

* * * * *